(12) United States Patent
Clark et al.

(10) Patent No.: US 9,365,483 B2
(45) Date of Patent: Jun. 14, 2016

(54) PROCESS FOR THE PRODUCTION OF ACETIC ACID AND DIMETHYL ETHER

(71) Applicant: BP CHEMICALS LIMITED, Middlesex (GB)

(72) Inventors: Thomas Edward Clark, Saltend (GB); John Glenn Sunley, East Yorkshire (GB)

(73) Assignee: BP CHEMICALS LIMITED, Middlesex (GB)

( * ) Notice: Subject to any disclaimer, the term of this patent is extended or adjusted under 35 U.S.C. 154(b) by 57 days.

(21) Appl. No.: 14/378,690

(22) PCT Filed: Feb. 22, 2013

(86) PCT No.: PCT/EP2013/053570
§ 371 (c)(1),
(2) Date: Aug. 14, 2014

(87) PCT Pub. No.: WO2013/124423
PCT Pub. Date: Aug. 29, 2013

(65) Prior Publication Data
US 2016/0031791 A1 Feb. 4, 2016

(30) Foreign Application Priority Data
Feb. 23, 2012 (EP) ..................................... 12250048

(51) Int. Cl.
*C07C 51/16* (2006.01)
*C07C 51/377* (2006.01)
*C07C 41/16* (2006.01)
*C07C 51/09* (2006.01)
*B01J 29/65* (2006.01)
*C07C 41/09* (2006.01)

(52) U.S. Cl.
CPC ............... *C07C 51/377* (2013.01); *B01J 29/65* (2013.01); *C07C 41/09* (2013.01); *C07C 41/16* (2013.01); *C07C 51/09* (2013.01)

(58) Field of Classification Search
None
See application file for complete search history.

(56) References Cited

U.S. PATENT DOCUMENTS 6,521,783 B1 2/2003 Wegman et al.
6,740,783 B1 5/2004 Jun et al.
2009/0326281 A1 12/2009 Appel et al.

FOREIGN PATENT DOCUMENTS

KR 2009131560 12/2009
WO WO 2011/027105 A1 3/2011

OTHER PUBLICATIONS

Seung-Chan Baeu, et al; "Influence of catalytic functionalities of zeolites on product selectivities in methanol conversion"; Energy & Fuels, vol. 23(2), pp. 593-598 (2009).
Khandan, N., et al; "Determining an optimum catalyst for liquid phase dehydration of methanol to dimethyl ether"; Applied Catalysis: General, vol. 349, Issues 1-2, pp. 6-12 (2008).

*Primary Examiner* — Patrick Lewis
(74) *Attorney, Agent, or Firm* — Nixon & Vanderhye P.C.

(57) ABSTRACT

Process for producing acetic acid and dimethyl ether by contacting a mixture of methanol and methyl acetate with a zeolite catalyst. The zeolite has a 2-dimensional channel system having at least one channel with a 10-membered ring and containing at least 5% of its cation exchange capacity occupied by one or more alkali metal cations.

18 Claims, No Drawings

PROCESS FOR THE PRODUCTION OF ACETIC ACID AND DIMETHYL ETHER

This application is the U.S. national phase of International Application No. PCT/EP2013/053570 filed Feb. 22, 2013 which designated the U.S. and claims priority to European Patent Application No. 12250048.1 filed Feb. 23, 2012, the entire contents of each of which are hereby incorporated by reference.

The present invention relates to a process for the co-production of acetic acid and dimethyl ether from a feed comprising methanol and methyl acetate in the presence of a zeolite catalyst. In particular, the process is conducted in the presence of an alkali metal exchanged zeolite catalyst.

Zeolites have been found useful to catalyse the dehydration of methanol to dimethyl ether. The use of ferrierite in its hydrogen form to catalyse the dehydration of methanol is described, for example, in the publications US 20090326281A, "Influence of catalytic functionalities of zeolites on product selectivities in methanol conversion" Seung-Chan Baek et al. Energy & Fuels, 2009, 23(2), pages 593-598 and "Determining an optimum catalyst for liquid-phase dehydration of methanol to dimethyl ether" Khandan, N et al. Applied Catalysis: General, vol. 349, Issues 1-2, 31 Oct. 2008, pages 6-12.

U.S. Pat. No. 6,740,783 describes an improved process for the preparation of dimethyl ether via the dehydration of a water-containing methanol feed in the presence of a zeolite catalyst in which zeolite the hydrogen cations are partially replaced with metal ions of Groups IA, IIA, IB and IIB of the Periodic Table or ammonium ions. The improvement is said to be that the catalyst is not deactivated by water present in the methanol feed.

Korean patent application, KR 2009131560A describes the preparation of dimethyl ether by dehydrating methanol at 200-350° C. and 1-50 atmospheres pressure in the presence of a ferrierite based catalyst or a catalyst obtained by the partial introduction of alkali metal and/or alkaline earth metal ions.

U.S. Pat. No. 6,521,783 describes a process in which acetic acid, methyl acetate, methanol, dimethyl ether and water is fed to a hydrolysis/dehydration reactor which contains an ester hydrolysis catalyst and an alcohol dehydration catalyst which can be the same or different. The alcohol dehydration catalyst can be selected from a solid acid, heteropolyacids, acidic zeolites, titania or silica promoted alumina, aluminium phosphate or tungsten oxide supported on silica-alumina. The ester hydrolysis catalyst can be selected from acidic ion-exchange resins, acidic gamma alumina, fluorinated alumina, sulphate or tungstate promoted zirconia, titania or silica promoted alumina, aluminium phosphate, tungsten oxide supported on silica-alumina, clays, supported mineral acids, zeolites or heteropolyacids. In an example relating to this process the nature of the catalyst is not identified.

WO 2011027105 describes the production of acetic acid and dimethyl ether from methanol and methyl acetate at a temperature of 140 to 250° C. in the presence of a zeolite catalyst. The zeolite has a 2-dimensional channel system comprising at least one channel having a 10-membered ring. The zeolites identified as being of this type include ferrierite, ZSM-35 and clinoptilolite. WO 2011027105 teaches that the zeolites suitable for use in such a process should contain only trace amounts of alkali or alkaline earth metals (0 to 0.2 wt % of the zeolite).

It has now been found that in the co-production of acetic and dimethyl ether by the dehydration and hydrolysis of methanol and methyl acetate in the presence of zeolite catalysts, zeolite catalysts such as ferrierite, with the passage of time, exhibit a loss of catalytic activity which results in a loss of productivity to the products, acetic acid and dimethyl ether. Such deactivation of the catalyst necessitates costly and time consuming regeneration processes to restore activity to the catalyst.

Typically, the dehydration and hydrolysis reaction is performed at temperatures of at least 140° C. to about 250° C. Generally, it is beneficial to perform the reaction at higher temperatures in order to achieve more attractive production rates. However, it has also been observed that zeolite catalysts useful for the reaction deactivate much more rapidly at higher reaction temperatures.

Furthermore, depending on their source, the methanol and/or methyl acetate feedstock may contain certain impurities such as acetone. It has now been found that the presence of such impurities, particularly at relatively high levels thereof, are deleterious to zeolite catalysts. Unless steps are taken to remove such impurities from the methanol and/or methyl acetate feedstocks prior to contact with the zeolite catalyst, their presence will enhance the rate at which the catalyst deactivates.

It would therefore be highly desirable to reduce the deactivation rate of zeolite catalysts for use in the co-production of acetic acid and dimethyl ether from methanol and methyl acetate feedstocks and, in particular to reduce the deactivation rate of such zeolite catalysts at high reaction temperatures and/or in the presence of impurities such as acetone.

It has now been found that these above-summarised deleterious effects can be unexpectedly ameliorated by carrying out the dehydration and hydrolysis reaction using zeolites which possess a 2-dimensional channel system comprising at least one channel with a 10-membered ring, and which is exchanged with one or more alkali metal cations.

In particular, it has been found that such zeolites exhibit increased resistance to deactivation at high reaction temperatures and/or in the presence of acetone. Advantageously, the result of employing zeolites having the afore-mentioned characteristics is an increase in the effective life of the zeolite catalyst in processes for the dehydration and hydrolysis of methanol and methyl acetate, and, in particular in those processes in which at least one of the feedstocks comprises acetone.

Accordingly, the present invention provides a process for the co-production of acetic acid and dimethyl ether from a mixture of methanol and methyl acetate which process comprises contacting in a reaction zone methanol feedstock and methyl acetate feedstock with a zeolite catalyst composition to produce acetic acid and dimethyl ether, said catalyst composition comprising a zeolite having a 2-dimensional channel system comprising at least one channel having a 10-membered ring and wherein at least 5 mol % of the zeolite's cation exchange capacity is occupied by one or more alkali metal cations.

Within the scope of the present description, the term "zeolite" is to be understood as a zeolite having a 2-dimensional channel system comprising at least one channel having a 10-membered ring.

Zeolites are well known materials of the aluminosilicate type with a three-dimensional structure of tetrahedra of aluminium and silicon which are co-ordinated tetrahedrally with oxygen atoms. These tetrahedral are joined together by means of oxygen atoms that they have in Common. Channel systems in zeolites are described as being 0-, 1-, 2- or 3-dimensional. The zeolites found to be useful in this invention possess a 2-dimensional channel system. The International Zeolite Association employs a three-letter code nomenclature to classify zeolites according to their framework structure type.

Information about zeolites, their framework structure types and channel systems is published in the Atlas of Zeolite Framework Types, C. H. Baerlocher, L. B. Mccusker and D. H. Olson, 6th Revised Edition, Elsevier, Amsterdam, 2007 and is also available at C. H. Baerlocher, L. B. Mccusker Database of Zeolite Structures: www.iza-online.org.

Zeolites are commercially available, for example, in the hydrogen or ammonium forms, from a number of commercial suppliers including Zeolyst International and Zeochem AG or they may be synthetically prepared using known techniques, as described, for example, in the afore-mentioned International Zeolite Association (IZA) website.

In the present invention, the 2-dimensional channel system of the zeolite comprises at least one channel having a 10-membered ring and may comprise one or more additional channels which have rings containing 4, 5, 6, 8, 10, 12, 14 or 16 members.

Preferably, the zeolite for use in the present invention has a 2-dimensional channel system having at least one channel which has a 10-membered ring and also at least one channel which has an 8-membered ring. Examples of such zeolites include zeolites of framework structures FER (for example, ferrierite, ZSM-35, ISI-6 and FU-9), HEU (for example, clinoptilolite), MFS (for example, ZSM-57), DAC (for example, dachiardite) and STI (for example, stilbite).

Other zeolites suitable for use in the present invention include zeolites having a framework structure selected from NES (for example, NU-87), MWW (for example, MCM-22) and TER (terranovaite).

Preferably, the zeolite has a framework structure selected from FER, HEU and MFS, and more preferably has the framework structure FER.

Suitably, zeolites for use in the present invention are ferrierite, ZSM-35, ISI-6, FU-9, ZSM-57 and clinoptilite. Preferably, the zeolite is selected from ferrierite and ZSM-35 and most preferably, the zeolite is ferrierite.

The 2-dimensional channel system of the zeolite may comprise interconnecting channels or non-interconnecting channels, preferably interconnecting channels.

The zeolite for use in the present invention is a zeolite in which one or more alkali metals occupy at least 5 mol % of its cation exchange capacity. By alkali metal is meant the metals of Group 1 of the Periodic Table and includes Li, Na, K, Rb, Cs and combinations thereof.

A preferred alkali metal is cesium.

The bulk silica to alumina molar ratio (herein also termed "SAR") of natural or synthetic zeolites will vary. The SAR of zeolites useful in the present invention may be in the range 10 to 90. Preferably, the zeolite has a SAR in the range 13 to 60, such as 17 to 55 and 20 to 55. The bulk silica to alumina molar ratio can be determined by any one of a number of chemical analysis techniques. Such techniques include x-ray fluorescence, atomic absorption and ICP (inductive coupled plasma). All will provide substantially the same silica to alumina molar ratio value.

In an embodiment of the present invention, the zeolite occupied with alkali metal cations is a ferrierite, preferably a ferrierite in the hydrogen form and which ferrierite has a SAR of from 10 to 90, for example of from 20 to 55.

The cation exchange capacity of the zeolite is determined by its alumina content. Each mole of aluminium ions substituted in tetrahedral positions of the zeolite framework generates a mole of negative charge on the framework. This charge is balanced by exchangeable cations. Since alkali metal cations are univalent, each mole of alkali metal cation incorporated via ion exchange replaces one mole of ammonium or hydrogen ions. The alkali metal content, the silica to alumina mole ratio and the degree of exchange are all related by the expression:

$$\% \text{ alkali metal exchange} = [\text{moles alkali metal}]/[(\text{moles Al}) \times 100]$$

These values are determined by any suitable analytical technique (such as elemental analysis, x-ray fluorescence, atomic absorption spectroscopy and inductive coupled plasma analytical techniques) which yields the amount of each element present in the dry alkali metal exchanged zeolite, resulting after exchange and washing with water, to remove all metal that has not been exchanged.

Zeolites for use in the present invention have at least 5 mol % of their cation exchangeable sites occupied by one or more alkali metal cations. This means that at least 5 mol % of the negative charge on the zeolite framework is balanced by alkali metal cations.

The cation exchangeable sites may be hydrogen or hydrogen precursor cations (such as ammonium ions). The zeolite catalyst for use in the present invention is manufactured by exchanging at least 5 mol % of its cation exchangeable sites by one or more alkali metal cations. The exchange may be carried out by known exchange techniques, such as by ion-exchange or impregnation techniques.

Where ion-exchange is desired to be used, the hydrogen or hydrogen precursor form of a zeolite may be exchanged with the desired alkali metal(s), simply by contacting it with an aqueous solution containing alkali metal cations which exchange with the hydrogen or hydrogen precursor cations. After contact of the zeolite with the aqueous solution of the alkali metal, the zeolite may be filtered to remove excess metal solution and the zeolite washed with water and then dried to produce a dry zeolite having alkali metal cations occupying at least a portion of its cation exchangeable sites.

Where impregnation is to be used, the hydrogen or hydrogen precursor form of a zeolite may be exchanged with the desired alkali metal(s), simply by contacting it with an aqueous solution containing alkali metal cations which exchange with the hydrogen or hydrogen precursor cations. After contacting of the zeolite with the aqueous solution containing alkali metal cations, the zeolite is dried to remove the water so as to produce a dry zeolite having alkali metal cations occupying at least a portion of its cation exchangeable sites.

Where a hydrogen precursor form of the zeolite was used in the exchange process, such as the ammonium form, subsequent to being dried, the zeolite may be calcined to convert ammonium cations to hydrogen cations. The resultant zeolite will be a zeolite having alkali metal cations occupying at least a portion of its cation exchangeable sites.

The exchange, optional washing, drying and, if desired, calcining steps may be repeated as many times as needed to achieve the desired cation exchange level.

Any suitable alkali metal salt may be used for the exchange solution of alkali metal cations. Examples of suitable alkali metal salts include, alkali metal acetates, alkali metal nitrates, alkali metal formates and alkali metal chlorides.

Zeolites for use in the present invention have at least 5 mol % of their cation exchange capacity occupied by one or more alkali metal cations. For example, at least 10 mol %, preferably at least 20 mol % of a zeolite's cation exchange capacity is occupied by one or more alkali metal cations.

The exchange of a zeolite's cation sites by alkali metal cations adjusts the acidity of the zeolite. The greater the degree of exchange, the lower the acidity of the zeolite. For the purposes of the present invention, zeolites may suitably have from 5 to 60 mol % of their cation exchange capacity occupied by one or more alkali metal cations, for example from 5 to 50 mol %, such as 10 to 50 mol %, 20 to 50 mol %, 15 to 40 mol %, 10 to 40 mol %, and 20 to 40 mol %.

In a specific embodiment of the present invention, from 5 to 50 mol % of a zeolite's cation exchangeable sites are occupied by one or more alkali metal cations, preferably the zeolite has a framework structure FER, and is more preferably ferrierite.

In a further embodiment of the present invention from 5 to 50 mol % of a zeolite's cation exchangeable sites are occupied by one or more alkali metal cations selected from cesium and/or rubidium, preferably, the zeolite has a framework structure FER, and is more preferably ferrierite.

Synthetic zeolites are typically prepared in the form of powders. Since a powder has no significant mechanical strength, its practical applications are limited. Mechanical strength can be conferred on a zeolite by forming a zeolite aggregate, for example, a shaped body, such as a pill or extrudate. An extrudate may be formed by extruding the zeolite in the presence of a binder and drying and calcining the resulting extrudate.

In addition to the zeolite, the catalyst composition may comprise at least one inorganic oxide binder. Examples of suitable inorganic oxide binders are silicas, aluminas, alumina-silicates, magnesium silicates, magnesium aluminium silicates, titanias, zirconias and clays.

Suitably, the inorganic oxide binder may be present in the catalyst composition in an amount in the range of 10 wt % to 90 wt % (based on total weight of zeolite and binder).

The zeolite catalyst composition is useful for the simultaneous dehydration and hydrolysis of a mixture of methanol and methyl acetate feedstocks to co-produce acetic acid and dimethyl ether.

In accordance with the present invention, methanol feedstock and methyl acetate feedstock are contacted with the zeolite catalyst composition to produce acetic acid and dimethyl ether products. The zeolite utilised in the present invention catalyses the dehydration of methanol and the hydrolysis of methyl acetate. The methanol dehydration and methyl acetate hydrolysis reactions can be represented by equations (1) and (2) respectively:

$$2CH_3OH \leftrightharpoons CH_3OCH_3 + H_2O \quad (1)$$

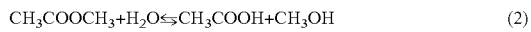

$$CH_3COOCH_3 + H_2O \leftrightharpoons CH_3COOH + CH_3OH \quad (2)$$

The methanol feedstock and the methyl acetate feedstock may be introduced into the reaction zone as a single feedstream. Preferably, however, the methanol and methyl acetate feedstocks are introduced into the reaction zone as separate feedstreams.

The molar ratio of methanol and methyl acetate may be any desired ratio but suitably, the molar ratio of methanol:methyl acetate is in the range 1:0.1 to 1:40, for example, 1:1 to 1:30.

The hydrolysis reaction requires water as a reactant. Water may be obtained from the dehydration reaction, which produces water in-situ. Preferably however, water is added to the process. Water may be added to the methanol and/or methyl acetate feedstocks or introduced into the reaction zone as a separate feed. Suitably, water may introduced into the reaction zone in an amount in the range 0.1 to 60 mol %, such as in the range 3 to 40 mol %, for example 5 to 30 mol % based on total feed of methyl acetate, methanol and water.

Methanol and methyl acetate are produced commercially. Typically, methanol is produced on an industrial scale by the catalytic conversion of synthesis gas. Methyl acetate is produced industrially, for example, via the esterification of acetic acid with methanol. Methyl acetate may also be produced by the anhydrous carbonylation of dimethyl ether in the presence of a zeolite catalyst.

Methanol and methyl acetate may be utilised in the present invention as pure feeds. However, depending on the source of the methanol and methyl acetate to be utilised in the present invention, low levels of by-product components, such as one or more of acetic acid, dimethyl ether, water and acetone may be present therein. Acetone may be present in methyl acetate derived from the anhydrous zeolite catalysed carbonylation of dimethyl ether and may also be in methanol produced by the catalytic conversion of synthesis gas. The total amount of acetone present in the methanol and methyl acetate produced by such processes will vary but may be, for example from 0.005 to 5 mol %.

Acetone has a similar boiling point to methyl acetate and methanol and therefore it is difficult to separate acetone from these components by simple distillation techniques. Acetone, even at relatively low (ppm) levels, has now been found to detrimental to the deactivation of certain zeolite catalysts, such as ferrierite, causing the catalysts to deactivate more quickly. It would therefore be highly desirable to provide catalysts which have reduced deactivation in processes for the conversion of methanol and methyl acetate to form dimethyl ether and acetic acid wherein at least one of the methanol and methyl acetate feedstocks comprises acetone.

Advantageously, the zeolites employed in the present invention have been found to be tolerant to acetone and maintain high catalytic activity without significant deactivation. In particular, the zeolites of the present invention have been found to be tolerant at acetone levels of from >0 to 5 mol % based on the total feed (including any recycles) to the reaction zone.

Thus, in an embodiment of the present invention, at least one of the methanol and methyl acetate feedstocks comprises acetone. Acetone may be introduced into the reaction zone in an amount of from >0 to 5 mol % based on total feed (including any recycles), such as in an amount of from 0.005 to 5 mol %, for example in an amount of from 0.5 to 5 mol % based on total feed (including any recycles).

Suitably, the methyl acetate feedstock for use in the present invention is derived from a process for the anhydrous zeolite catalysed carbonylation of dimethyl ether to produce methyl acetate and may suitably comprise acetone in an amount of from >0 to 5 mol %, for example 0.005 to 5 mol %, such as 0.5 to 5 mol % (based on total feed, including recycles, to the reaction zone). Alternatively and/or additionally, the methanol feedstock for use in the present invention may be derived from a process for the catalytic conversion of synthesis gas to produce methanol and may suitably comprise acetone in an amount of from >0 to 5 mol %, for example 0.005 to 5 mol %, such as 0.5 to 5 mol % (based on total feed, including recycles, to the reaction zone).

Where acetone is present in at least one of the methyl acetate and methanol feedstocks, preferably water is introduced into the reaction zone in an amount in the range 0.1 to 60 mol %, such as in the range 3 to 40 mol %, for example in the range 5 to 30 mol %, based on the total feed to the reaction zone (including any recycles).

In an embodiment of the present invention, acetone is present in at least one of the methanol and methyl acetate feedstocks, for example in an amount of from >0 to 5 mol %, such as in an amount of from 0.005 to 5 mol %, for example 0.5 to 5 mol % based on total feed (including any recycles) to the reaction zone, the zeolite employed has the framework structure FER, for example ferrierite and the zeolite has from 5 to 60 mol %, for example 10 to 50 mol % of its cation exchangeable sites occupied by one or more alkali metal cations, and, in particular one or more of cesium and sodium cations.

In another embodiment, acetone is present in at least one of the methanol and methyl acetate feedstocks, for example in an amount of from >0 to 5 mol %, such as in an amount of from 0.005 to 5 mol %, for example 0.5 to 5 mol % based on total feed (including any recycles) to the reaction zone, the zeolite employed has the framework structure FER, for example ferrierite and the zeolite has from 5 to 60 mol %, for example 10 to 50 mol % of its cation exchangeable sites occupied by one or more alkali metal cations, and, in particular one or more of cesium and sodium cations and water is introduced into the reaction zone in an amount in the range from 0.1 to 60 mol %, such as 3 to 40 mol %, for example 5 to 30 mol % based on the total feed to the reaction zone (including any recycles).

A diluent such as an inert gas, for example, nitrogen and helium may also be a feed to the process.

The process may be carried out in the reaction zone as a vapour phase or as a liquid phase process, for example as a fixed bed process or a slurry phase process.

Where the process is operated as a vapour phase process, the feedstock(s), prior to entering the reaction zone, may be in the liquid phase. However, prior to contact with the zeolite, the liquid phase components should be volatilised, for example, by use of a pre-heater.

The process is suitably carried out at temperatures in the range 170° C. to 280° C. The zeolites utilised in the present invention have been found to be particularly beneficial at temperatures in the range 190° C. to 240° C.

In a specific embodiment of the present invention, the process to produce acetic acid and dimethyl ether is carried out by contacting methanol feedstock and methyl acetate feedstock, optionally at least one of the methanol and methyl acetate feedstocks comprises acetone, for example in an amount of from >0 to 5 mol % based on total feed (including any recycles) at a temperature in the range 170° C. to 280° C., and in particular in the range 190° C. to 240° C., such as 220° C. to 240° C., with a zeolite of framework structure FER, such as ferrierite, and which has 5 to 60%, for example 5 to 50%, such as 10 to 50% of its cation exchangeable sites occupied by one or more alkali metal cations, such as one or more alkali metal cations selected from cesium and sodium cations.

The process may be carried out at atmospheric pressure or at pressures greater than atmospheric. Where the process is carried out in the liquid phase, it is preferred to operate the process at a total reaction pressure which is sufficient to maintain the dimethyl ether product in solution. Suitably, therefore, the pressure may be at least 40 barg, such as 40 to 100 barg, suitably 40 to 60 barg. Where the process is carried out in the vapour phase, suitable operating pressures are in the range atmospheric to 30 barg, such as 2 to 20 barg, for example 2 to 15 barg.

The gas hourly space velocity (GHSV) is suitably in the range 500 to 40,000 h$^{-1}$, such as 1,000 to 25,000 for example 1,000 to 15,000h$^{-1}$.

The liquid hourly space velocity (LHSV) is suitably in the range 0.2 to 20, such as in the range 0.5 to 10 h$^{-1}$, for example, 0.5 to 5 or in the range 2 to 8 h$^{-1}$.

The process may be operated as either a continuous or a batch process, preferably as a continuous process.

The product stream of the present invention comprises acetic acid and dimethyl ether. The product stream may optionally further comprise water, unreacted methanol and unreacted methyl acetate. The acetic acid and dimethyl ether may be recovered from the product stream by conventional purification methods, such as by distillation. Dimethyl ether will generally be recovered as an overhead from a distillation column, and the acetic acid will typically be recovered as a bottoms fraction from the column together with any methyl acetate, methanol and water. The acetic acid can be separated from these components by further distillation. The recovered dimethyl ether may be sold or may be used as a feedstock to carbonylation processes for the production of methyl acetate. The acetic acid may be sold or may be used as a feed in other downstream processes, such as the manufacture of vinyl acetate or ethyl acetate.

The invention is now illustrated with reference to the following non-limiting Examples.

EXAMPLE 1

Preparation of Cs-Ferrierite 20 g of NH$_4$-ferrierite (SAR of 20) (ex Zeolyst International), 1.97 g of CsNO$_3$ (ex Sigma Aldrich, 99% purity) and 48 ml of de-ionised water were stirred together for 16 hours at ambient temperature, dried under vacuum at a pressure of 250 mbar and at a temperature of 80° C., and then heated for 20 hours at 110° C., followed by calcining in air for 3 hours at 500° C. to yield H-ferrierite with 37 mol % of its cation sites occupied by cesium.

EXAMPLE 2

Preparation of Cs-Ferrierites

A series of catalysts were prepared in accordance with the method of example 1 except that the amounts of CsNO$_3$ used were those as shown in Table 1 below so as to prepare H-ferrierites with 9.2 mol % and 18.5 mol % of the cation sites occupied by cesium.

EXAMPLE 3

Preparation of Odium, Potassium and Rubidium Ferrierites

The method of example 1 was repeated using the amounts of sodium, potassium and rubidium nitrates as specified in Table 1 below so as to prepare H-ferrierites with 9.2 mol %, 18.5 mol % and 37 mol % of its cation sites occupied by sodium, potassium or rubidium.

TABLE 1

| Example | Alkali Metal | Amount of metal nitrate (g) | | |
| --- | --- | --- | --- | --- |
| | | 9.2 mol % | 18.5 mol % | 37 mol % |
| Ex. 2 | Cs | 0.49 | 0.98 | 1.97 (Ex. 1) |
| Ex. 3 | Na | 0.22 | 0.43 | 0.86 |
| Ex. 3 | K | 0.26 | 0.51 | 1.02 |
| Ex. 3 | Rb | 0.37 | 0.75 | 1.49 |

EXAMPLE 4

Dehydration/Hydrolysis Using H-Ferrierite 0.015 g of a ferrierite in its hydrogen form (SAR 20, ex Zeolyst International) was pressed and sieved to particles of 100 to 160 microns, loaded into a reactor and covered with 150 microliters of carborundum. Nitrogen and helium gases were flowed into the reactor at a rate of 4.4 ml/min and 0.9 ml/min respectively to provide a gas hourly space velocity of 16,000/h. The pressure was increased to 10 barg and the reactor temperature adjusted to 180° C. A vapour feed comprising 50 mol % methyl acetate, 30 mol % methanol and 20 mol % water was passed into the catalyst bed at a gas hourly space velocity of 4,000/h and held at a reactor temperature of 180° C. for 48 hours after which the temperature was increased to 220° C. for 120 hours and then reduced to 180° C. for 36 hours. The exit stream from the reactor was periodically analysed on an Interscience Trace gas chromatograph equipped with two TCD detectors and one FID detector and comprised acetic acid and dimethyl ether. The deactivation of the H-ferrierite catalyst was calculated by the loss in its activity over 120 hours at 220° C.

EXAMPLE 5

Dehydration/Hydrolysis Using Alkali Metal Ferrierites

Example 4 was repeated except that the ferrierite was replaced by each of the alkali metal loaded ferrierite catalysts prepared in accordance with examples 1 to 3. The loss in activity of the alkali metal loaded ferrierite catalysts was calculated by the loss in activity over 120 hours at 220° C.

The deactivation rates of the alkali metal loaded ferrierite catalysts relative to H-ferrierite were calculated from the expression:

Deactivation rate=[loss in activity of H-ferrierite]/
[loss in activity of alkali metal loaded ferrierite].

The relative deactivation rates (to H-ferrierite) of the catalysts at the different alkali metal exchange levels are shown in Table 2 below. The higher the relative deactivation rate, the slower the rate of catalyst deactivation.

TABLE 2

| Alkali Metal | Relative Deactivation Rates at alkali metal exchange levels | | |
|---|---|---|---|
| | 9.2 mol % | 18.5 mol % | 37 mol % |
| Na | 1.2 | 1.7 | 3.2 |
| K | 1.8 | 1.3 | 5.7 |
| Rb | 1.7 | 2.8 | n/a |
| Cs | 2.3 | 3.9 | 12.5 |

As can be seen from an inspection of Table 2, each of the alkali metal ferrierites is materially more robust to deactivation than H-ferrierite, and, in particular, the higher the level of alkali metal loading, the more stable the catalyst.

EXAMPLE 6

Dehydration/Hydrolysis in the Presence of Acetone

H-ferrierite (SAR 20, manufacturer Zeolyst International Inc) and each of the catalysts prepared in examples 1 to 3 were used as a catalyst in the dehydration/hydrolysis of methanol and methyl acetate. Prior to use, 0.015 g of a catalyst was pressed and sieved to particles of 100 to 160 microns, loaded into a reactor and covered with 150 microliters of carborundum. Nitrogen and helium gases were flowed into the reactor at a rate of 4.4 ml/min and 0.9 ml/min respectively to provide a gas hourly space velocity of 16,000/h. The pressure was increased to 10 barg and the reactor temperature adjusted to 180° C. A vapour feed comprising 47.5 mol % methyl acetate, 28.5 mol % methanol, 19 mol % water and 5 mol % acetone was passed into the catalyst bed at a gas hourly space velocity of 4,000/h and held at a reactor temperature of 180° C. for 36 hours after which the temperature was increased to 200° C. for 72 hours, then increased to 220° C. for a further 72 hours and subsequently reduced to 180° C. for 48 hours. The exit stream from the reactor was periodically analysed on an Interscience Trace gas chromatograph equipped with two TCD detectors and one FID detector and comprised acetic acid and dimethyl ether. The deactivation of each catalyst was calculated by the loss in its activity over 144 hours at 200-220° C. The deactivation rate of the catalysts (relative to H-ferrierite) at different alkali metal exchange levels is shown in Table 3 below. The higher the relative deactivation rate, the slower the rate of catalyst deactivation.

TABLE 3

| Alkali Metal | Relative Deactivation Rate at alkali metal exchange levels | | |
|---|---|---|---|
| | 9.2 mol % | 18.5 mol % | 37 mol % |
| Na | 1.7 | 3.1 | 10.3 |
| K | 1.7 | 2.5 | 9.5 |
| Rb | 1.5 | 2.2 | n/a |
| Cs | 1.5 | 3.2 | 10.3 |

As can be seen from Table 3, the alkali metal ferrierites are significantly less susceptible to deactivation in the presence of acetone compared to H-ferrierite. In particular, significant tolerance to acetone is demonstrated at higher metal loadings.

EXAMPLE 7

Preparation of Cs Ferrierites

Example 1 was repeated using a $NH_4$-ferrierite of SAR 55 (ex Zeolyst International) and amounts of 0.66 g, 0.88 g and 1.09 g $CsNO_3$ were added so as to prepare H-ferrierites of SAR 55 with 30 mol %, 40 mol % and 50 mol % of its cation sites occupied by cesium.

EXAMPLE 8

Dehydration/Hydrolysis Reaction

The dehydration/hydrolysis process of example 4 was repeated using a H-ferrierite having a SAR of 55 and each of the cesium loaded ferrierite catalysts prepared in accordance with example 7. The deactivation rates of the cesium ferrierites (relative to the H-ferrierite) at the various cesium exchange levels are shown in Table 4 below. The higher the relative deactivation rate, the slower the rate of catalyst deactivation.

TABLE 4

| Alkali Metal | Relative Deactivation Rate at alkali metal exchange levels | | |
|---|---|---|---|
| | 30 mol % | 40 mol % | 50 mol % |
| Cs | 2.5 | 2.5 | 3.1 |

This example demonstrates that at high silica:alumina molar ratios, the alkali metal loaded ferrierite is significantly less susceptible to deactivation compared to H-ferrierite.

EXAMPLE 9

Dehydration/Hydrolysis in the Presence of Acetone

The dehydration/hydrolysis reaction of example 6 was repeated using a H-ferrierite having a SAR of 55 and each of the cesium loaded ferrierite catalysts prepared in accordance with example 7. The deactivation rates of the cesium ferrierites (relative to H-ferrierite) at the various cesium exchange levels are shown in Table 5 below. The higher the relative deactivation rate, the slower the rate of catalyst deactivation.

TABLE 5

| Alkali Metal | Relative Deactivation Rate at alkali metal exchange levels | | |
|---|---|---|---|
| | 30 mol % | 40 mol % | 50 mol % |
| Cs | 3.2 | 3.3 | 4.3 |

This example demonstrates that the cesium ferrierites are significantly less susceptible to deactivation in the presence of acetone compared to H-ferrierite.

EXAMPLE 10

Preparation of Catalysts B to E

A series of ferrierites loaded with varying amounts of cesium were prepared from a ferrierite in hydrogen form of SAR of 20 (referred to as Catalyst A) and cesium acetate (ex Sigma Aldrich). 5 g of the hydrogen form ferrierite and an amount of cesium acetate as shown in Table 6 were added to 12 microliters of deionised water and stirred at room temperature for 16 hours. Water was removed from the stirred mixture under vacuum using a rotary evaporator operated at 150 mbar and 60° C., and then dried at 110° C. for 20 hours to produce a solid. The solid was calcined in air at 500° C. for 3 hours. The calcined products were ferrierite in hydrogen form loaded with cesium in an amount of either 20, 30, 40 or 50 mol % (referred to as Catalysts B to E respectively).

TABLE 6

| Catalyst | Cs acetate/ (g) | Cs/ mol % |
|---|---|---|
| B | 0.2622 | 20 |
| C | 0.3934 | 30 |
| D | 0.5245 | 40 |
| E | 0.6556 | 50 |

EXAMPLE 12

Dehydration/Hydrolysis Reaction in the Presence of Acetone 0.015 g of each of catalysts A to E was pressed and sieved to particles of size 100 to 160 microns. The catalyst particles were loaded onto a metal sinter (pore size of 20 microns) in a reactor tube and the remainder of the reactor was filled with 150 microliters of carborundum. To start-up the reactor, nitrogen and helium were flowed into the reactor at a rate of 4.4 ml/min and 0.9 ml/min respectively. The reactor was pressurised to 10 barg and heated to a temperature of 180° C. After this pretreatment, the nitrogen and helium were shut off and a vapour feed comprising 72 mol % methyl acetate, 7.5 mol % methanol, 0.5 mol % acetone and 20 mol % water was introduced into the reactor at a total gas hourly space velocity of 4000/h for 46 hours after which time the temperature was increased to 210° C. for 110 hours and then reduced to 180° C. for 45 hours. The temperature was then increased from 180° C. to 210° C. for 111 hours and then reduced to 180° C. for 55 hours. The temperature was then increased from 180° C. to 230° C. for 116 hours and then reduced to 180° C. for 35 hours. The temperature was then increased from 180° C. to 250° C. for 97 hours and then reduced to 180° C. for 35 hours. The exit stream from the reactor was periodically analysed on an Interscience Trace gas chromatograph equipped with two TCD detectors and one FID detector and comprised acetic acid and dimethyl ether. Table 7 shows the deactivation rates obtained for each of the catalysts A to E for the reaction periods conducted at temperatures of 210° C. (second period), 230° C. and 250° C. The deactivation rates were calculated as the % loss in space time yield (STY) per day for the each of the products, dimethyl ether and acetic acid.

TABLE 7

| Catalyst | Cs (mol %) | Temperature (° C.) | Deactivation Rate Dimethyl Ether | Deactivation Rate Acetic Acid |
|---|---|---|---|---|
| A | 0 | 210 | 1.5 | 1.3 |
| B | 20 | 210 | 1.1 | 0.5 |
| C | 30 | 210 | 0.6 | 0.2 |
| D | 40 | 210 | 0.3 | −0.4 |
| E | 50 | 210 | 0.9 | −0.4 |
| A | 0 | 230 | 5.9 | 6.1 |
| B | 20 | 230 | 3.6 | 3.1 |
| C | 30 | 230 | 2.6 | 2.3 |
| D | 40 | 230 | 2.1 | 1.5 |
| E | 50 | 230 | 2.6 | 1.4 |
| A | 0 | 250 | 13.8 | 10.4 |
| B | 20 | 250 | 8.9 | 6.0 |
| C | 30 | 250 | 6.0 | 3.5 |
| D | 40 | 250 | 5.3 | 1.7 |
| E | 50 | 250 | 4.7 | 2.1 |

It can be seen from an inspection of Table 7 that each of the cesium loaded catalysts (Catalysts B to E) have a materially reduced deactivation rate compared to Catalyst A (H-ferrierite).

EXAMPLE 13

Effect of Acetone

This Example illustrates dehydration-hydrolysis reactions of methanol and methyl acetate feeds, with acetone and without acetone, carried out in the presence of a H-ferrierite catalyst. 3.2 mm extrudates of a H-ferrierite (SAR 20) composited with 20 wt % alumina were crushed and sieved to obtain particles of size 250-500 microns.

0.3 g of the catalyst particles were loaded into each of the four reactors of a 4-reactor channel micro-reactor unit. The micro-reactor unit comprised 4 separate Hastelloy U-shaped reactor tubes of internal diameter of 6 mm, each with their own dedicated gas (controlled using separate mass-flow control valves) and liquid feed streams. Each liquid feed stream was administered to a reactor in vapour form using a syringe drive pump. Prior to contacting a catalyst bed, the vapourised feed was mixed with 80 mol % inert gas over an inert silicon carbide pre-bed before passing it over the catalyst bed at a total gas hourly space velocity (GHSV) of about 10,500 hr$^{-1}$.

A liquid feed composition of 50 mol % methyl acetate, 30 mol % methanol and 20 mol % water was fed into reactor 1. Liquid feed compositions of methyl acetate, methanol, water with acetone added to a molar concentration of 0.5%, 1.0% and 3.0% were fed to reactors 2, 3 and 4 respectively.

Each reactor was maintained at a reaction temperature of 180° C. by means of a fluidised sand-bath heater. Each reactor had an independent pressure control and the total reaction pressure of each reactor was maintained at 10 barg. Each reaction was allowed to continue for about 450 hours. The product stream from each reactor was heated in a series of heated ovens and trace-heated lines to maintain a gas phase product stream for analysis. The pressure of each product stream was let-down to atmospheric pressure prior to analysis. Each product stream was analysed periodically by gas chromatography (Agilent MicroGC) to provide composition data of the feed and product components. The effect of acetone on catalyst performance for the period 50 to 400 hours on stream is shown in Table 8 below. Table 8 provides the deactivation rates obtained, calculated as space time yield (STY) loss per day of each of the reaction products, dimethyl ether and acetic acid.

TABLE 8

| Reactor | Acetone (mol %) | DME Deactivation Rate | Acetic Acid Deactivation Rate |
|---|---|---|---|
| 1 | no acetone | 2.7 | 4.3 |
| 2 | 0.5 | 2.8 | 5.0 |
| 3 | 1.0 | 5.0 | 6.1 |
| 4 | 3.0 | 8.3 | 9.9 |

As can clearly be seen from Table 8, the presence of acetone in feeds to a dehydration/hydrolysis reaction is harmful to a ferrierite catalyst as it leads to an increase in the rate of deactivation of the catalyst.

The invention claimed is:

1. A process for the co-production of acetic acid and dimethyl ether from a mixture of methanol and methyl acetate which process comprises contacting in a reaction zone methanol feedstock and methyl acetate feedstock with a zeolite catalyst composition to produce acetic acid and dimethyl ether, said catalyst composition comprising a zeolite having a 2-dimensional channel system comprising at least one channel having a 10-membered ring and wherein at least 5 mol % of the zeolite's cation exchange capacity is occupied by one or more alkali metal cations.

2. A process according to claim 1 wherein the zeolite further comprises at least one channel having an 8-membered ring.

3. A process according to claim 2 wherein the zeolite has a framework structure selected from the group consisting of FER, HEU, MFS, DAC, STI, NES, MWW and TER.

4. A process according to claim 3 wherein the zeolite has the framework structure FER and is ferrierite.

5. A process according to claim 1 wherein the alkali metal is cesium.

6. A process according to claim 1 wherein at least 10% of the zeolite's cation exchange capacity is occupied by one or more alkali metal cations.

7. A process according to claim 1 wherein from 5 to 60%, of the zeolite's cation exchange capacity is occupied by one or more alkali metal cations.

8. A process according to claim 1 wherein the zeolite has a SAR in the range 10 to 90.

9. A process according to claim 1 wherein at least one of the methanol feedstock and methyl acetate feedstock comprises acetone.

10. A process according to claim 9 wherein acetone is present in at least one of the methanol feedstock and methyl acetate feedstock in a total amount of from >0 to 5 mol % based on the total feedstock including any recycles.

11. A process according to claim 1 wherein the methyl acetate feedstock is derived from a process for the zeolite catalysed carbonylation of dimethyl ether to produce methyl acetate.

12. A process according to claim 1 wherein the process is carried out at a temperature in the range from 170 to 280° C.

13. A process according to claim 1 wherein the catalyst composition comprises at least one inorganic oxide binder.

14. A process according to claim 1 wherein the methanol to methyl acetate molar ratio is in the range 1:0.1 to 1:40.

15. A process according to claim 1 wherein water is introduced into the reaction zone.

16. A process according to claim 15 wherein water is introduced into the reaction zone in an amount in the range 0.1 to 60 mol % based on the total feed to the reaction zone including any recycles.

17. A process according to claim 1 wherein the process is operated in the vapour phase.

18. A process according to claim 17 wherein the process is operated at a total pressure in the range 2 to 20 barg.

* * * * *